(12) United States Patent
Fujii et al.

(10) Patent No.: US 8,007,545 B2
(45) Date of Patent: Aug. 30, 2011

(54) DEODORANT COMPOSITIONS

(75) Inventors: Motoko Fujii, Wakayama (JP); Akira Ishikawa, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/543,162

(22) Filed: Oct. 5, 2006

(65) Prior Publication Data

US 2007/0117739 A1    May 24, 2007

(30) Foreign Application Priority Data

Nov. 18, 2005   (JP) ................. 2005-334800

(51) Int. Cl.
*C11D 3/00* (2006.01)
*C11D 3/37* (2006.01)

(52) U.S. Cl. .................... 8/115.51; 510/499

(58) Field of Classification Search ............ 510/499; 8/115.51
See application file for complete search history.

(56) References Cited

U.S. PATENT DOCUMENTS

| | | | |
|---|---|---|---|
| 5,417,867 A * | 5/1995 | Mikami et al. | 252/8.61 |
| 5,470,509 A | 11/1995 | Pancheri | |
| 5,514,302 A * | 5/1996 | Brown | 510/280 |
| 5,616,552 A * | 4/1997 | Yoshihara et al. | 510/490 |
| 5,705,472 A * | 1/1998 | Hayes et al. | 510/423 |
| 6,699,828 B1 * | 3/2004 | de Buzzaccarini et al. | 510/372 |
| 2003/0114331 A1 * | 6/2003 | Baker et al. | 510/276 |
| 2004/0144406 A1 * | 7/2004 | Garabedian et al. | 134/26 |

FOREIGN PATENT DOCUMENTS

| | | |
|---|---|---|
| DE | 2354517 | 5/1975 |
| EP | 0451002 A2 | 10/1991 |
| FR | 2339395 | 8/1977 |
| GB | 1541396 | 2/1979 |
| GB | 2281076 A | 2/1995 |
| WO | WO 96/32180 A1 | 10/1996 |
| WO | WO 97/45189 A1 | 12/1997 |
| WO | WO-03/039496 A1 | 5/2003 |

OTHER PUBLICATIONS

English language abstract of JP 2003-116972 (Apr. 22, 2003).
English language abstract of JP 2004-049889 (Feb. 19, 2004).
English language abstract of JP 1135243 (Dec. 7, 1999).
European Office Action issued Aug. 3, 2010 for Application No. 06 020 932.7.
Chinese Office Action, dated Feb. 12, 2011, for Chinese Application No. 200610162724.1.

* cited by examiner

*Primary Examiner* — Milton I Cano
*Assistant Examiner* — Thuy-Ai N Nguyen
(74) *Attorney, Agent, or Firm* — Birch, Stewart, Kolasch & Birch, LLP

(57) ABSTRACT

The present invention relates to a deodorant composition including (a) a polyhydroxyamine compound having a specific structure and/or a salt thereof, and (b) a penetrant including at least one substance selected from the group consisting of (b1) a nonionic surfactant having a specific structure, (b2) a surfactant having a residue of a monosaccharide, etc., (b3) a nonionic organic solvent having a log P value of from 0 to 4; and (b4) an amine oxide type or carbobetaine type amphoteric surfactant; as well as a deodorizing method using the deodorant composition. The deodorant composition of the present invention is capable of reducing or eliminating a composite odor derived from sweat smell and aldehydes, readily producing a water-based deodorant, and is safe even upon contacting with a human body.

3 Claims, No Drawings

DEODORANT COMPOSITIONS

This application claims foreign priority under 35 USC 119(a-d) to Japanese application having serial number 2005-334800.

FIELD OF THE INVENTION

The present invention relates to deodorant compositions and deodorizing methods.

BACKGROUND OF THE INVENTION

Deodorants are used together with an aromatizing agent to reduce uncomfortable odors or smells and, therefore, play an important role for comfortable human lives. Recent needs for deodorization are changing from aromatizing agents for masking malodors with a strong aroma to subtly-odorous or odorless deodorants capable of reducing or eliminating odors or smells themselves.

Also, there is an increasing tendency that clothes that are not in direct contact with the skin are repeatedly put on without immediate laundering. On the other hand, much care is taken about odors or smells from such clothes. Most of uncomfortable odors or smells encountered in the environment of human life are due to a composite odor. Therefore, it has been demanded to provide deodorants capable of effectively acting on such a composite odor.

Hitherto, there are known techniques for reducing or eliminating specific malodors. However, there are known few techniques that are effective to the composite odors or smells.

For example, JP 2001-40581A discloses a liquid deodorant using a cationic surfactant or an amphoteric surfactant in combination with a chelating agent for reducing or eliminating sweat smell or tobacco smell. JP 2001-70423A discloses a liquid deodorant using a deodorizing base agent such as perfumes in combination with a cationic surfactant and a specific solvent for reducing or eliminating sweat smell. However, these conventional liquid deodorants are unsatisfactory in deodorizing performance against aldehydes, etc.

JP 2001-178806A discloses a deodorant composition using a deodorizing base agent containing an extract obtained from plants as a main component, in combination with a perfume, ethanol and a surfactant for suppressing a rotten or putrid odor. JP 2004-176225A discloses a deodorizing fiber capable of reducing or eliminating ammonia smell, etc., which is treated with a treating agent composed of a betaine type amphoteric compound, a nonionic surfactant and an anionic surfactant. However, these conventional deodorizing products are also unsatisfactory in deodorizing performance against sweat small or aldehydes.

In JP 2004-49889A, it is described that an anionic surfactant containing a salt of at least one compound selected from the group consisting of triethanol amine, tris(hydroxymethyl) aminomethane, etc., is effective to suppress such a composite odor in which lower fatty acids and amines coexist. However, the anionic surfactant composed of such amine salts is insufficient in deodorizing effect on aldehydes and tends to exhibit a poor solubility in water, and is therefore unsuitable for preparation of deodorant compositions.

In JP 2001-95907A, it is described that an organic dibasic acid or a salt thereof is effective to deodorize lower fatty acids such as acetic acid and isovaleric acid, ammonia, amines such as trimethylamine, etc. However, the organic dibasic acid or the salt thereof is unsatisfactory in deodorizing effect on aldehydes.

In JP 2001-97838A, it is described that ethanolamine is effective to deodorize unsaturated aldehydes such as nonenal that is one of substances causing an aged smell from persons of middle or advanced age. However, the effect of ethanolamine on sweat smell, etc., is not clear, and further ethanolamine is stimulus and, therefore, unsuitable for use in such a configuration that the compound tends to be contacted with a human body.

JP 2003-533588A discloses a deodorizing composition containing cyclodextrin in which a primary amine compound is used as a buffer. However, in JP 2003-533588A, there is no description that a specific combined use of the primary amine compound and a nonionic compound exhibits a high deodorizing effect.

Under these circumstances, there is a demand for developing a deodorant which is not only capable of reducing or eliminating a composite odor derived from, especially, sweat smell and aldehydes, but also is safe to a human body.

SUMMARY OF THE INVENTION

The present invention relates to the following aspects [1] and [2]:

[1] A deodorant composition having:

(a) a polyhydroxyamine compound represented by the general formula (1):

wherein $R^1$ is a hydrogen atom, an alkyl group having 1 to 5 carbon atoms or a hydroxyalkyl group having 1 to 5 carbon atoms; $R^2$ is a hydrogen atom, an alkyl group having 1 to 6 carbon atoms or a hydroxyalkyl group having 1 to 5 carbon atoms; and $R^3$ and $R^4$ are respectively an alkanediyl group having 1 to 5 carbon atoms, and may be the same or different from each other,
and/or a salt thereof, and (b) a penetrant comprising at least one substance selected from the group consisting of:

(b1) a nonionic surfactant represented by the general formula (2):

wherein $R^5$ is an alkyl or alkenyl group having 10 to 22 carbon atoms; $R^6$ is a hydrogen atom or an alkyl group having 1 to 3 carbon atoms; Z is —O— or —COO—; EO is an oxyethylene group; PO is an oxypropylene group; s and t are average molar numbers of addition of EO and PO, respectively, with the proviso that a sum of s and t (s+t) is from 5 to 15; and (EO) and (PO) may be respectively either random-added or block-added, and the order of addition of (EO) and (PO) is optional;

(b2) a surfactant represented by the general formula (3):

wherein $R^7$ is a linear or branched alkyl, alkenyl or alkylphenyl group having 8 to 18 carbon atoms; $R^8$ is an alkenyl group having 2 to 4 carbon atoms; G is a residue of a monosaccharide, a monosaccharide derivative or an oligosaccharide which is obtained by removing a hydrogen atom of a hydroxyl group contained therein; and x is an average molar number of addition of $OR^8$ ranging from 5 to 20;

(b3) a nonionic organic solvent having a log P value of from 0 to 4; and (b4) an amine oxide type or carbobetaine type amphoteric surfactant.

[2] A deodorizing method of reducing or eliminating an odor generated from an objective having a solid surface, including the step of allowing the deodorant composition as described in the above aspect [1] to adhere to the solid surface of the objective.

DETAILED DESCRIPTION OF THE INVENTION

The present invention relates to a deodorant composition which is capable of reducing or eliminating a composite odor derived from sweat smell or aldehydes, readily producing a water-based deodorant therefrom, and is safe even upon contacting with a human body, as well as a deodorizing method using the deodorant composition.

The present inventors have found that specific polyhydroxyamines are effective to reduce or eliminate a composite odor derived from sweat smell or aldehydes, have a less stimulus to a human body, and can exhibit an enhanced deodorizing performance when used in combination with a specific surfactant or a specific nonionic organic solvent.

That is, the present invention relates to the following aspects [1] and [2]:

[1] A deodorant composition comprising:

(a) a polyhydroxyamine compound represented by the general formula (1):

wherein $R^1$ is a hydrogen atom, an alkyl group having 1 to 5 carbon atoms or a hydroxyalkyl group having 1 to 5 carbon atoms; $R^2$ is a hydrogen atom, an alkyl group having 1 to 6 carbon atoms or a hydroxyalkyl group having 1 to 5 carbon atoms; and $R^3$ and $R^4$ are respectively an alkanediyl group having 1 to 5 carbon atoms, and may be the same or different from each other, and/or a salt thereof, and (b) a penetrant comprising at least one substance selected from the group consisting of:

(b1) a nonionic surfactant represented by the general formula (2):

$$R^5-Z-[(EO)_s/(PO)_t]-R^6 \quad (2)$$

wherein $R^5$ is an alkyl or alkenyl group having 10 to 22 carbon atoms; $R^6$ is a hydrogen atom or an alkyl group having 1 to 3 carbon atoms; Z is —O— or —COO—; EO is an oxyethylene group; PO is an oxypropylene group; s and t are average molar numbers of addition of EO and PO, respectively, with the proviso that a sum of s and t (s+t) is from 5 to 15; and (EO) and (PO) may be respectively either random-added or block-added, and the order of addition of (EO) and (PO) is optional;

(b2) a surfactant represented by the general formula (3):

$$R^7-(OR^8)_x G \quad (3)$$

wherein $R^7$ is a linear or branched alkyl, alkenyl or alkylphenyl group having 8 to 18 carbon atoms; $R^8$ is an alkenyl group having 2 to 4 carbon atoms; G is a residue of a monosaccharide, a monosaccharide derivative or an oligosaccharide which is obtained by removing a hydrogen atom of a hydroxyl group contained therein; and x is an average molar number of addition of $OR^8$ ranging from 5 to 20;

(b3) a nonionic organic solvent having a log P value of from 0 to 4; and (b4) an amine oxide type or carbobetaine type amphoteric surfactant.

[2] A deodorizing method for reducing or eliminating an odor generated from an objective having a solid surface, comprising the step of allowing the deodorant composition as described in the above aspect [1] to adhere to the solid surface of the objective.

The deodorant composition of the present invention contains a polyhydroxyamine compound represented by the following general formula (1):

and/or a salt thereof (a) (hereinafter occasionally referred to merely as "polyhydroxyamine compounds (a)") as a main component.

Polyhydroxyamine Compounds (a):

In the general formula (1), $R^1$ is a hydrogen atom, an alkyl group having 1 to 5 carbon atoms or a hydroxyalkyl group having 1 to 5 carbon atoms.

The alkyl group having 1 to 5 carbon atoms as $R^1$ may be either linear or branched. Examples of the alkyl group as $R^1$ include methyl, ethyl, n-propyl, isopropyl, various butyl groups and various pentyl groups. Examples of the hydroxyalkyl group having 1 to 5 carbon atoms as $R^1$ include hydroxymethyl, 2-hydroxyethyl, 2-hydroxypropyl, 3-hydroxypropyl, 2-hydroxybutyl, 3-hydroxybutyl and 4-hydroxybutyl.

Among these groups as $R^1$, in view of good deodorizing performance and good availability, preferred are a hydrogen atom, methyl, ethyl, hydroxymethyl and 2-hydroxyethyl, and more preferred are a hydrogen atom, hydroxymethyl and 2-hydroxyethyl.

In the general formula (1), $R^2$ is a hydrogen atom, an alkyl group having 1 to 6 carbon atoms or a hydroxyalkyl group having 1 to 5 carbon atoms.

The alkyl group having 1 to 6 carbon atoms as $R^2$ may be either linear, branched or cyclic. Examples of the alkyl group as $R^2$ include methyl, ethyl, n-propyl, isopropyl, various butyl groups, various pentyl groups, various hexyl groups, cyclopentyl and cyclohexyl.

Examples of the hydroxyalkyl group having 1 to 5 carbon atoms as $R^2$ include the same groups as described for $R^1$.

Among these groups as $R^2$, in view of good deodorizing performance and good availability, preferred are a hydrogen atom, alkyl groups having 1 to 3 carbon atoms and hydroxyethyl, and more preferred is a hydrogen atom.

In the general formula (1), $R^3$ and $R^4$ are respectively an alkanediyl group having 1 to 5 carbon atoms, and may be the same or different from each other. Examples of the preferred alkanediyl group having 1 to 5 carbon atoms as $R^3$ and $R^4$ include methylene, ethylene, trimethylene, propane-1,2-diyl and tetramethylene. Among these alkanediyl groups, especially preferred is a methylene group.

Specific examples of the polyhydroxyamine compounds (a) include 2-amino-1,3-propanediol, 2-amino-2-methyl-1,3-propanediol, 2-amino-2-ethyl-1,3-propanediol, 2-amino-2- hydroxymethyl-1,3-propanediol, 2-amino-2-hydroxyethyl-1,3-propanediol, 4-amino-4-hydroxypropyl-1,7-heptanediol, 2-(N-ethyl)amino-1,3-propanediol, 2-(N-ethyl)amino-2-hydroxymethyl-1,3-propanediol, 2-(N-decyl)amino-1,3-propanediol, 2-(N-decyl)amino-2-hydroxymethyl-1,3-propanediol, and salts of these compounds with hydrochloric acid, sulfuric acid, nitric acid, phosphoric acid, carbonic acid, etc.

Among these polyhydroxyamine compounds, in view of a good deodorizing performance, etc., especially preferred is at least one compound selected from the group consisting of 2-amino-1,3-propanediol, 2-amino-2-methyl-1,3-propanediol, 2-amino-2-ethyl-1,3-propanediol, 2-amino-2-hydroxymethyl-1,3-propanediol, 2-amino-2-hydroxyethyl-1,3-propanediol and salts of these compounds with an acid such as hydrochloric acid.

When the polyhydroxyamine compound represented by the general formula (1) is used in the form of a salt thereof with hydrochloric acid, etc., the pH of the salt may be adjusted by adding a base thereto. Examples of the base used include sodium hydroxide, potassium hydroxide, magnesium hydroxide and calcium hydroxide, as well as monoethanol amine, diethanol amine, triethanol amine, methyl ethanol amine and dimethyl ethanol amine. Among these bases, preferred are sodium hydroxide and potassium hydroxide.

The above polyhydroxyamine compounds (a) may be used alone or in the form of a mixture of any two or more thereof. Meanwhile, the polyhydroxyamine compounds (a) may be produced by an ordinary method.

The polyhydroxyamine compounds (a) can exhibit a good deodorizing performance against a composite odor derived from fatty acids, aldehydes and amines even when used either alone or in the form of a mixture thereof. The deodorizing performance of the polyhydroxyamine compounds (a) can be further enhanced by using the compounds (a) in combination with a penetrant (b) containing at least one substance selected from the group consisting of a nonionic surfactant (b1) represented by the below-mentioned general formula (2), a surfactant (b2) represented by the below-mentioned general formula (3), a nonionic organic solvent (b3) having a log P value of from 0 to 4, and an amine oxide type or carbobetaine type amphoteric surfactant (b4).

The penetrant (b) serves as a base agent for improving a penetrability of the polyhydroxyamine compounds (a) into fiber products, etc., or a wettability thereof to a hard surface for the purpose of allowing the polyhydroxyamine compounds (a) to exhibit an enhanced deodorizing performance.

More specifically, the penetrant (b) have not only the effect of suppressing a vaporization of odor components usually adhered onto a solid surface of fiber products such as suits, sweaters, curtains and sofas, etc., but also the effect of stably dispersing the polyhydroxyamine compounds (a) as a deodorizing ingredient therein, thereby improving a penetrability or contacting property of the compounds to the solid surface of the fiber products, etc., to further enhance the deodorizing performance. Thus, even though the objective to be deodorized is such a hard surface, the penetrant (b) allows the polyhydroxyamine compounds (a) to exhibit an improved wettability thereto, thereby enhancing a deodorizing performance of the resultant composition.

Penetrant (b)

The penetrant (b) used in the present invention is preferably composed of at least one substance selected from the group consisting of the nonionic surfactant (b1) represented by the below-mentioned general formula (2), the surfactant (b2) represented by the below-mentioned general formula (3) and an amine oxide type or carbobetaine type amphoteric surfactant (b4), and more preferably composed of the nonionic surfactant (b1) represented by the below-mentioned general formula (2). However, the use of polyoxyalkylene group-added type castor oils or hardened castor oils are undesirable since these compounds are poor in property for penetrating the polyhydroxyamine compounds (a) into the fiber products, etc.

Nonionic Surfactant Represented by the Following General Formula (2) [Component (b1)]

In the general formula (2), $R^5$ is an alkyl or alkenyl group having 10 to 22 carbon atoms; $R^6$ is a hydrogen atom or an alkyl group having 1 to 3 carbon atoms; Z is —O— or —COO—; EO is an oxyethylene group; PO is an oxypropylene group; s and t are average molar numbers of addition of EO and PO, respectively, and t is preferably a number of not less than 0 but less than 3 and more preferably from 0 to 2 with the proviso that a sum of s and t (s+t) is from 5 to 15. When the nonionic surfactant contains both of (EO) and (PO), the (EO) and (PO) may be respectively either random-added or block-added, and the order of addition of (EO) and (PO) is optional.

The component (b1) includes, for example, compounds having the following structure:

wherein $R^5$ is the same as defined above; $R^9$ is an ethylene group and/or a propylene group; and n is an average molar number of addition of $OR^9$ ranging from 5 to 15.

In the compounds having the above structure, when $R^9$ contains a propylene group, the average molar number of addition of the propylene group is preferably less than 3.

As the component (b1), in view of improving a deodorizing performance of the resultant composition, especially preferred is at least one compound selected from the group consisting of a polyoxyethylene (average molar number of addition of oxyethylene groups: s=6 to 12) lauryl ether, a polyoxyethylene (average molar number of addition of oxyethylene groups: s=5 to 12) monoalkyl (secondary hydrocarbon group having 12 to 14 carbon atoms) ether, and a polyoxyethylene (average molar number of addition of oxyethylene groups: s=6 to 12) laurate methyl ether.

Surfactant Represented by the Following General Formula (3) [Component (b2)]

In the general formula (3), $R^7$ is a linear or branched alkyl, alkenyl or alkylphenyl group having 8 to 18 carbon atoms; $R^8$ is an alkenyl group having 2 to 4 carbon atoms; G is a residue of a monosaccharide, a monosaccharide derivative or an oligosaccharide which is obtained by removing a hydrogen atom of a hydroxyl group contained therein; and x is an average molar number of addition of $OR^8$ ranging from 5 to 20.

Examples of the monosaccharide as G in the general formula (3) include aldopentoses such as glucose, fructose, galactose, mannose, xylose, arabinose, ribose, talose, idose, altrose, allose and gulose, and aldohexoses.

The monosaccharide derivative includes compounds obtained by ring-opening the monosaccharide by a reduction reaction thereof, and compounds obtained by further subjecting the ring-opened compound to a ring opening reaction.

The oligosaccharide preferably contains 5 or less constitutional monosaccharide units and more preferably 2 to 3 constitutional monosaccharide units. The glycoside bond between the monosaccharide units is preferably (1→2), (1→4) or (1→6). The type of the glycoside bond may be either α-type or β-type. Examples of the oligosaccharide include homo-oligosaccharides such as gluco-oligosaccharides, galacto-oligosaccharides, manno-oligosaccharides and fructo-oligosaccharides, oligosaccharides constituted from pentose and hexose, and oligosaccharides constituted from different kinds of hexoses. Among these compounds, preferred are oligosaccharides constituted from glucose repeating units.

Examples of the preferred residue of G include a glucose residue, a sorbose residue and a sorbitan residue.

As the component (b2), in view of improving the deodorizing performance, there is preferably used at least one compound selected from the group consisting of a polyoxyethylene (average molar number of addition of oxyethylene groups: x=5 to 20 and preferably 5 to 15; parentheses in the subsequent descriptions have the same meaning) monolaurate sorbitan, a polyoxyethylene (x=10 to 20) monostearate sorbitan and a polyoxyethylene (x=10 to 20) monooleate sorbitan.

Nonionic Organic Solvent Having a log P Value of 0 to 4 [Component (b3)]

The component (b3) is a nonionic organic solvent having a log P value of 0 to 4, preferably 0 to 3.5, more preferably 0 to 3 and still more preferably 0 to 2. The component (b3) is preferably such a compound containing no alkyl group or containing an alkyl group having 1 to 9 carbon atoms.

Here, the "Log P value" means a logarithm of a 1-octanol/water partition coefficient of the compound, i.e., a ratio between equilibrium concentrations of the solute in the respective solvents under a partition equilibrium condition in which the solute compound is dissolved in a two-liquid phase solvent system composed of 1-octanol and water, and is generally expressed by a logarithm with a base of 10 ("log P"). That is, the log P value is an index of a hydrophilicity (hydrophobicity) of the compound. The larger the log P value, the more hydrophobic the compound becomes, whereas the smaller the log P value, the more hydrophilic the compound becomes.

As to the log P value, reference should be made, for example, to databases available from Daylight Chemical Information Systems Inc. (Daylight CIS) in which log P values of many compounds are described. If no actual log P value of the compound is present, the value can be calculated from the program "C LOG P" (available from Daylight CIS) and the like. Among them, the program "C LOG P" is most suitably used owing to a high reliability.

In the program "C LOG P", the "calculated log P (C log P)" value obtained according to fragment approach of Hansch, Leo is output together with an actual value of log P, if any. The fragment approach is based on a chemical structure of the compound and takes into consideration the number of atoms and the type of chemical bond thereof (A. Leo, "Comprehensive Medicinal Chemistry", Vol. 4, C. Hansch, P. G. Sammems, J. B. Taylor and C. A. Ramsden, Eds., p. 295, Pergamon Press, 1990). This C log P value is an estimated value that is most general and reliable at the present time. Therefore, when the compound selected has no actual log P value, the C log P value thereof can be suitably used instead. In the present invention, there may be used either the actual log P value or the Clog P value calculated according to the program "C LOG P". However, the actual value, if any, is preferably used.

Examples of the suitable component (b3) include 2-ethylhexane-1,3-diol, 2,5-dimethylhexane-2,5-diol, nonane-1,9-diol, 2-methyloctane-1,8-diol, 1,4-cyclohexane dimethanol, monoethylene glycol monopropyl ether, monoethylene glycol monobutyl ether, diethylene glycol monobutyl ether, triethylene glycol monobutyl ether, monoethylene glycol monohexyl ether, diethylene glycol monohexyl ether, triethylene glycol monohexyl ether, monoethylene glycol monooctyl ether, diethylene glycol monooctyl ether, triethylene glycol monooctyl ether, monoethylene glycol monophenyl ether, diethylene glycol monophenyl ether, triethylene glycol monophenyl ether, monoethylene glycol monobenzyl ether, diethylene glycol monobenzyl ether, triethylene glycol monobenzyl ether, tripropylene glycol monomethyl ether, monopropylene glycol monopropyl ether, dipropylene glycol monopropyl ether, monopropylene glycol monobutyl ether, dipropylene glycol monobutyl ether, tripropylene glycol monobutyl ether, monopropylene glycol monophenyl ether, glyceryl ether monobutyl ether, glyceryl ether monopentyl ether, glyceryl ether monohexyl ether, glyceryl ether monoheptyl ether, glyceryl ether monooctyl ether, 2-ethylhexyl glyceryl ether, hexaglyceryl monolaurate, hexaglyceryl monomyristate, hexaglyceryl monostearate and hexaglyceryl monooleate.

Among these compounds as the component (b3), in view of improving the deodorizing performance, especially preferred is at least one compound selected from the group consisting of diethylene glycol monobutyl ether, triethylene glycol monophenyl ether, glyceryl ether monopentyl ether, glyceryl ether monohexyl ether, glyceryl ether monooctyl ether and 2-ethylhexyl glyceryl ether.

Amine Oxide Type or Carbobetaine Type Amphoteric Surfactant [Component (b4)]

Examples of the amine oxide type amphoteric surfactant include alkyldimethylamine oxides and alkylamidopropylamine-N,N-dimethyl-N-oxides which contain a substituted or unsubstituted alkyl group having 8 to 18 carbon atoms.

Examples of the carbobetaine type amphoteric surfactant include alkylaminoacetic acid betaines, alkyldimethylaminoacetic acid betaines and alkylamidopropylamine-N,N-dimethyl-N-acetic acid betaines which contain a substituted or unsubstituted alkyl group having 8 to 18 carbon atoms.

Among these surfactants, preferred is at least one compound selected from the group consisting of amine oxide type amphoteric surfactants represented by the general formula (4):

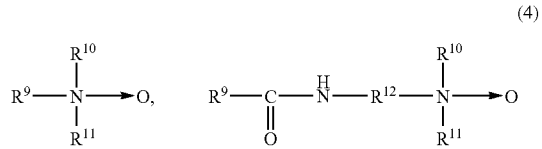

and carbobetaine type amphoteric surfactants represented by the general formula (5):

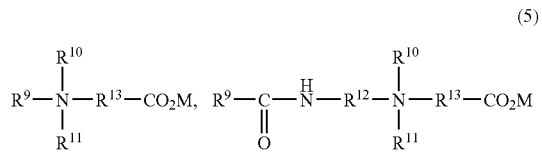

In the general formulae (4) and (5), $R^9$ is a substituted or unsubstituted alkyl or alkenyl group having 8 to 18 carbon atoms; $R^{10}$ and $R^{11}$ are respectively methyl, ethyl or a hydroxyalkyl group having 2 or 3 carbon atoms; $R^{12}$ is a substituted or unsubstituted alkanediyl group having 2 to 5 carbon atoms; and $R^{13}$ is a substituted or unsubstituted alkanediyl group having 1 to 5 carbon atoms. Examples of the substituent group of these groups include an alkyl group, an amino group and a halogen atom.

In the general formulae (4) and (5), $R^9$ is preferably a substituted or unsubstituted alkyl or alkenyl group having 10 to 16 carbon atoms and more preferably a substituted or unsubstituted alkyl group having 10 to 16 carbon atoms.

Specific examples of the amine oxide type amphoteric surfactant represented by the general formula (4) include lauryldimethylamine oxide and laurylamidopropylamine-N,N-dimethyl-N-oxide. Specific examples of the carbobetaine type amphoteric surfactant represented by the general formula (5) include lauryldimethylaminoacetic acid betaine and laurylamidopropylamine-N,N-dimethyl-N-acetic acid betaine.

The penetrant (b) preferably contains the component (b1) and/or the component (b2) in combination with the component (b3) in order to enhance the effect of the polyhydroxyamine compounds (a).

The weigh ratio of a sum of the components (b1) and (b2) to the component (b3) $\{[(b1)+(b2)]/(b3)\}$ is preferably from 10/1 to 1/10, more preferably from 5/1 to 1/5 and still more preferably from 3/1 to 1/3.

The penetrant (b) preferably contains the component (b1) and/or the component (b2) and/or the component (b4) in combination with the component (b3) in order to enhance the effect of the polyhydroxyamine compounds (a).

The weigh ratio of a sum of the components (b1), (b2) and (b4) to the component (b3) $\{[(b1)+(b2)+(b4)]/(b3)\}$ is preferably from 10/1 to 1/10, more preferably from 5/1 to 1/5 and still more preferably from 3/1 to 1/3.

The contents of the polyhydroxyamine compounds (a) and the penetrant (b) in the deodorant composition of the present invention may be appropriately controlled according to a concentration of malodor to be reduced or eliminated, a configuration of the composition used, etc.

The content of the polyhydroxyamine compounds (a) in the deodorant composition is usually 0.02% by weight or more, preferably from 0.02 to 1% by weight, more preferably from 0.02 to 0.9% by weight and still more preferably from 0.02 to 0.8% by weight.

The total content of the penetrant components (b1) to (b4) in the deodorant composition is usually 0.01% by weight or more, preferably from 0.01 to 1% by weight, more preferably from 0.01 to 0.9% by weight and still more preferably from 0.01 to 0.8% by weight.

In order to enhance the effect of the polyhydroxyamine compounds (a), the blending ratio (weigh ratio) of the polyhydroxyamine compounds (a) to the penetrant (b) [(a)/(b)] is preferably from 10/1 to 1/10, more preferably from 8/1 to 1/8, still more preferably from 5/1 to 1/5 and further still more preferably from 4/1 to 1/4 and most preferably from 3/1 to 1/3.

In the deodorant composition of the present invention, the balance of the composition other than the polyhydroxyamine compounds (a) and the penetrant (b) may be composed of water. The water used in the composition is preferably water obtained by removing ion components from distilled water, ion-exchanged water, etc.

The deodorant composition of the present invention may also contain, if required, other components such as polyhydric alcohols, other surfactants, other deodorants, various generally added solvents, oil agents, gelling agents, salts such as sodium sulfate and N,N,N-trimethyl glycin, pH modifiers, antioxidants, antiseptic agents, bactericides or antimicrobial agents, perfumes, pigments and ultraviolet absorbers, unless the addition thereof adversely affects the aimed effects of the present invention.

The polyhydric alcohols serve for suppressing vaporization of odor components adhered to the solid surface, allowing the polyhydroxyamine compounds (a) as a deodorizing ingredient to be stably dispersed, and improving the contact between the deodorizing ingredient and the odor components to enhance a deodorizing performance thereof.

Examples of the polyhydric alcohols usable in the composition of the present invention include glycerol, ethylene glycol, propylene glycol, 1,3-propanediol, butanediol, diethylene glycol, dipropylene glycol, polyethylene glycol and polypropylene glycol. Among these polyhydric alcohols, preferred are diethylene glycol and dipropylene glycol.

The content of the polyhydric alcohols used in the composition may vary depending upon a concentration of malodor to be reduced or eliminated, a configuration of the composition used, etc., and is usually 0.001% by weight or more, preferably from 0.001 to 30% by weight and more preferably from 0.005 to 10% by weight.

Also, as the solvent, there may be used water and lower alcohols having 3 to 4 carbon atoms such as ethanol and isopropanol.

The pH of the deodorant composition of the present invention is preferably controlled to the range of from 6.0 to 9.5. When the pH of the deodorant composition is 6.0 or more, the composition can exhibit an excellent effect on sweat smell or aldehydes, and when the pH of the deodorant composition is 9.5 or less, the composition can exhibit an excellent effect on amines.

In view of enhancing the effect on whole composite odors derived from sweat smell, aldehydes, etc., and reducing stimulus to the skin, the pH of the deodorant composition is preferably from 6.5 to 9.5 and more preferably from 6.8 to 9.0.

The pH of the deodorant composition of the present invention may be controlled by adding an acid such as hydrochloric acid or an alkali such as sodium hydroxide thereto.

The configuration of use of the deodorant composition of the present invention may be a liquid, a gel, a powder or a solid such as granules. The liquid deodorant composition of the present invention may be applied especially to spraying solutions, lotions, etc., and the content of water used in the liquid deodorant composition is preferably 70% by weight or more, more preferably from 70 to 99.9% by weight and still more preferably from 80 to 99.8% by weight. The deodorant composition of the present invention is more preferably used in the form of a water-based deodorant composition which is filled in a mist-type spray container and controlled so as to be sprayed therefrom in an amount of 0.1 to 1 mL per one spraying stroke. As the spray container, there may be used known spray containers such as a trigger spray container (of a straight hydraulic type or an accumulator type) and a dispenser type pump spray container.

The deodorant composition in the form of a gel or a solid is suitable for being used partially in human body, hair, pets, etc. In addition, the deodorant composition of the present invention may also be used in a stationary condition, for example, as a filter for air cleaners or the like by impregnating or spraying papers, nonwoven fabrics, etc., with the deodorant composition.

The objectives to which the deodorizing method using the deodorant composition of the present invention is applicable, are not particularly limited as long as they have a solid surface. For example, the deodorant composition of the present invention may be applied to objectives having a solid surface, e.g., fiber products such as fabrics, clothes and carpets and other articles such as dishes, garbage boxes, cooking tables, interior floors, ceilings and walls to effectively reduce or eliminate odors generated from the objectives. In particular, the deodorant composition of the present invention is more effectively applied to such objectives having a broad surface area to be deodorized such as fiber products.

EXAMPLES

The following examples further describe and demonstrate embodiments of the present invention. The examples are given solely for the purpose of illustration and are not to be construed as limitations of the present invention.

Examples 1 to 13 and Comparative Examples 1 and 2

Preparation of Deodorant Composition

The deodorant compositions having respective blending ratios as shown in Table 1, were prepared. Meanwhile, "Ploxel BDN" (available from Avecia K.K.; 10% aqueous solution) was used as an antibacterial agent, and the pH of the respective deodorant compositions was adjusted to 8.0 by adding a 1N hydrochloric acid aqueous solution or a 1/10N sodium hydroxide aqueous solution thereto.

The components represented by the respective symbols in Table 1 are as follows.
Component (a)
a-1: 2-Amino-2-hydroxymethyl-1,3-propanediol
a-2: 2-Amino-2-methyl-1,3-propanediol
a-3: 2-Amino-1,3-propanediol
Component (b)
  Component (b1)
  b1-1: Polyoxyethylene (average molar number of addition of oxyethylene groups: 8) lauryl ether
  b1-2: Polyoxyethylene (average molar number of addition of oxyethylene groups: 9) monoalkyl (secondary hydrocarbon group having 12 to 14 carbon atoms) ether
  b1-3: Polyoxyethylene (average molar number of addition of oxyethylene groups: 9) laurate methyl ether
  Component (b2)
  b2-1: Polyoxyethylene (average molar number of addition of oxyethylene groups: 6) monolaurate sorbitan
  b2-2: Polyoxyethylene (average molar number of addition of oxyethylene groups: 15) monooleate sorbitan
  Component (b3)
  b3-1: Glyceryl ether monohexyl ether (log P: 1.1)
  b3-2: 2-Ethylhexyl monoglyceryl ether (log P: 2.0)
  b3-3: Diethylene glycol monobutyl ether (log P: 0.6)
  Component (b4)
  b4-1: Laurylamidopropylamine-N,N-dimethyl-N-oxide
  b4-2: Lauryldimethylamine oxide
  b4-3: Laurylamidopropylamine-N,N-dimethyl-N-acetic acid betaine
  b4-4: Lauryldimethylamineacetic acid betaine
Other Components
  b'-1: Polyoxyethylene (average molar number of addition of oxyethylene groups: 40) hardened castor oil The deodorant composition obtained in Example 1 to 13 and Comparative Examples 1 and 2 were blended with 0.01% of a perfume to prepare a deodorant composition. Meanwhile, as the perfume, there was used a formulated perfume composed of 5 parts of ethyl cinnamate, 10 parts of linalyl acetate, 15 parts of Lyral, 10 parts of hexyl cinnamic aldehyde, 10 parts of Pearide, 20 parts of phenyl ethyl aldehyde, 10 parts of cedar alcohol and 20 parts of limonene.

<Preparation of Objective to be Deodorized>

A 10 ppm isovaleric acid ethanol solution in substitution for sweat smell or a 1% nonanal ethanol solution in substitution for aldehyde smell as an odor component was sprayed onto a cotton knitted fabric (10 cm×10 cm) one time using a spray vial ("No. 6" available from Maruemu Co., Ltd.), and then dried for 30 min, thereby preparing a test specimen.

<Deodorizing Method>

The test specimen thus obtained by the above method was sprayed with the respective deodorant compositions having blending ratios shown in Table 1 six times using a spray vial ("No. 6" available from Maruemu Co., Ltd.), and then dried for 1 h.

<Evaluation of Deodorizing Performance>

The thus treated test specimen was smelled by total 10 panelists including five males and five females of the age of thirties. The deodorizing performance was evaluated according to the following 6 ratings using an odor intensity representation method to obtain an average value of the evaluation points. The results are shown in Table 1.

[Evaluation Criteria for Odor Intensity]
0: No odor
1: Faintly sensible odor (detectable threshold level)
2: Kind of odor was recognizable, and readily sensible weak odor (recognizable threshold level)
3: Odor was apparently sensible
4: Strong odor
5: Unbearable strong odor

TABLE 1

|  | Examples |  |  |  |  |  |  |  |  |  |
|---|---|---|---|---|---|---|---|---|---|---|
|  | 1 | 2 | 3 | 4 | 5 | 6 | 7 | 8 | 9 | 10 |
|  | Composition (weigh %) |  |  |  |  |  |  |  |  |  |
| Component (a) |  |  |  |  |  |  |  |  |  |  |
| a-1 | 0.05 |  |  | 0.05 |  |  |  | 0.05 |  | 0.05 |
| a-2 |  | 0.05 |  |  | 0.05 |  | 0.05 |  |  |  |
| a-3 |  |  | 0.05 |  |  | 0.05 |  |  | 0.05 |  |
| Component (b) |  |  |  |  |  |  |  |  |  |  |
| b1-1 | 0.1 |  | 0.2 |  |  |  |  |  |  |  |
| b1-2 |  |  |  |  | 0.2 |  |  |  | 0.1 |  |
| b1-3 |  |  |  |  |  |  |  | 0.2 |  |  |
| b2-1 |  | 0.2 |  |  |  |  |  |  |  |  |
| b2-2 |  |  |  |  |  |  | 0.2 |  |  |  |
| b3-1 | 0.1 |  |  | 0.2 |  |  |  |  |  |  |
| b3-2 |  |  |  |  |  |  |  |  |  | 0.1 |

TABLE 1-continued

|   | | | | | | | | | |
|---|---|---|---|---|---|---|---|---|---|
| b3-3 | | | | | | | | 0.3 | |
| b4-1 | | | | | | | | | 0.1 |
| b4-2 | | | | | | | | | |
| b4-3 | | | | | | | | | |
| b4-4 | | | | | | | | | |
| b'-1 | | | | | | | | | |
| Antibacterial agent | 0.1 | 0.1 | 0.1 | 0.1 | 0.1 | 0.1 | 0.1 | 0.1 | 0.1 | 0.1 |
| Perfume | 0.01 | 0.01 | 0.01 | 0.01 | 0.01 | 0.01 | 0.01 | 0.01 | 0.01 | 0.01 |
| pH modifier | Amount required for adjusting the pH to 8.0 | | | | | | | | | |
| Ion-exchanged water | Bal* | Bal* | Bal* | Bal* | Bal* | Bal* | Bal* | Bal* | Bal* | Bal* |

Evaluation

| | | | | | | | | | | |
|---|---|---|---|---|---|---|---|---|---|---|
| Isovaleric acid smell | 1.2 | 1.8 | 1.2 | 2.2 | 1.2 | 1.8 | 1.2 | 1.2 | 2.5 | 1.8 |
| Nonanal smell | 1.2 | 2.5 | 2.5 | 2.5 | 2.0 | 2.5 | 2.5 | 1.2 | 2.5 | 2.5 |

|   | Examples | | | Comparative Examples | |
|---|---|---|---|---|---|
|   | 11 | 12 | 13 | 1 | 2 |

Composition (weigh %)

Component (a)

|   | 11 | 12 | 13 | 1 | 2 |
|---|---|---|---|---|---|
| a-1 | | | | 0.05 | |
| a-2 | 0.05 | 0.05 | | | |
| a-3 | | | 0.05 | | |

Component (b)

|   | 11 | 12 | 13 | 1 | 2 |
|---|---|---|---|---|---|
| b1-1 | | | | | |
| b1-2 | | | | | |
| b1-3 | | | | | |
| b2-1 | | | | 0.2 | |
| b2-2 | | | | | |
| b3-1 | | | | | |
| b3-2 | | | | | |
| b3-3 | | | | | |
| b4-1 | | | | | |
| b4-2 | 0.2 | | | | |
| b4-3 | | 0.1 | | | |
| b4-4 | | | 0.1 | | |
| b'-1 | | | | | 0.2 |
| Antibacterial agent | 0.1 | 0.1 | 0.1 | 0.1 | 0.1 |
| Perfume | 0.01 | 0.01 | 0.01 | 0.01 | 0.01 |
| pH modifier | Amount required for adjusting the pH to 8.0 | | | | |
| Ion-exchanged water | Bal* | Bal* | Bal* | Bal* | Bal* |

Evaluation

|   | 11 | 12 | 13 | 1 | 2 |
|---|---|---|---|---|---|
| Isovaleric acid smell | 1.8 | 2.0 | 2.0 | 4.5 | 3.5 |
| Nonanal smell | 2.5 | 2.5 | 2.5 | 4.5 | 3.5 |

Note:
*Balance

From Table 1, it was confirmed that the deodorant compositions obtained in Comparative Examples 1 and 2 were insufficient in deodorizing performance against isovaleric acid smell (substitute for sweat smell) and nonanal smell (substitute for aldehyde smell), whereas the deodorant compositions obtained in Examples 1 to 13 exhibited a high deodorizing performance against any of isovaleric acid smell and nonanal smell, and still maintained a scent of the perfume blended therein.

INDUSTRIAL APPLICABILITY

The deodorant composition of the present invention is capable of reducing or eliminating a composite odor derived from sweat smell and aldehydes, readily producing a water-based deodorant, and is safe even upon contacting with a human body, and further exhibits an excellent deodorizing effect on a composite odor adhered onto a solid surface of fiber products, etc. Therefore, the deodorant composition of the present invention can be suitably used as a deodorant composition for reducing or eliminating a composite odor adhered to objectives having a solid surface, e.g., fiber products such as fabrics, clothes and carpets and other articles such as dishes, garbage boxes, cooking tables, and interior floors, ceilings and walls.

Further, according to the deodorizing method of the present invention, a composite odor derived from sweat smell and aldehydes can be reduced or eliminated in a simple and effective manner.

What is claimed is:
1. A deodorizing method for reducing or eliminating an odor generated from an object having a solid surface, consisting essentially of the step of allowing a water-based deodorant composition to adhere to the solid surface of the object and then drying;
wherein the pH of said deodorant composition is 6.8 to 9.0;
said deodorant composition comprises:
(a) 2-amino-2-hydroxymethyl-1,3-propanediol and/or a salt thereof, and

(b) a penetrant comprising a nonionic organic solvent having a log P value of from 0 to 4 and
at least one nonionic surfactant selected from the group consisting of (i) a polyoxyethylene lauryl ether wherein the polyoxyethylene has an average molar number of addition of oxyethylene groups of 6 to 12, and (ii) a polyoxyethylene monoalkyl ether wherein the polyoxyethylene has an average molar number of addition of oxyethylene groups of 5 to 12 and the monoalkyl has a secondary hydrocarbon group having 12 to 14 carbon atoms;
water in a content of from 70 to 99.9% by weight, and
a weight ratio of a sum of the nonionic surfactant to the nonionic organic solvent in the penetrant (b) is from 10/1 to 1/10;
wherein a content of the polyhydroxyamine compound and/or the salt thereof (a) is from 0.02 to 1% by weight, and a content of the penetrant (b) is from 0.01 to 1% by weight.

2. The deodorizing method according to claim 1, wherein the object having the solid surface is a fiber product.

3. The deodorizing method according to claim 1, wherein the odor is derived from sweat smell or aldehydes.

* * * * *